United States Patent [19]

Patel

[11] Patent Number: 5,391,345
[45] Date of Patent: Feb. 21, 1995

[54] SURGICAL WRAP

[75] Inventor: Harish Patel, Norfolk, Mass.

[73] Assignee: The Kendall Company, Mansfield, Mass.

[21] Appl. No.: 220,857

[22] Filed: Mar. 31, 1994

[51] Int. Cl.$^6$ ............................................. B32B 31/04
[52] U.S. Cl. .................................. 264/258; 26/18.5;
26/18.6; 28/100; 206/440; 422/1; 602/75;
602/76
[58] Field of Search ...................... 602/75, 76; 28/100,
28/158, 163; 264/258; 206/339, 440; 422/1;
26/18.5, 18.6

[56] References Cited

U.S. PATENT DOCUMENTS 2,081,370  5/1937  Secrist .

Primary Examiner—James J. Bell
Attorney, Agent, or Firm—Alvin Isaacs

[57] ABSTRACT

An eight ply surgical wrap used for wrapping over and around a bandage to secure it in place, after it has been applied to a patients limb. The surgical wrap is formed from a single ply gauze fabric which is first bleached and washed, then folded into a four ply and then the fabric is overfed into a hot bath which agitates the fabric to make the yarns absorbent, fluffy, and elastic. The fabric is then passed through embossing rolls. The hot bath and the embossing roll causes the yarns to distort into an oblique and serpentine arrangement. The four ply fabric is then folded in a series of folds to create an eight ply fabric, that is highly absorbent, and because of the manner in which the fabric is folded, the surgical wrap is free of exposed selvege edges eliminating any chance of the selvege edges forming or causing a binding effect in the wrap.

5 Claims, 3 Drawing Sheets

SURGICAL WRAP

DESCRIPTION OF THE INVENTION

1. Field of Invention

This invention relates to surgical wraps used to apply over and to secure bandages in place on a patients limb. More particularly it relates to an eight ply surgical wrap roll which is absorbent, elastic and whereby there are no exposed selvege edges.

2. Prior Art

Surgical wraps are generally made from cotton yarns woven into a gauze fabric which should be soft and pliable for use as an overwrap of bandages. The surgical wrap must permit the wound to be aerated and be capable of absorbing wound exudates when covering a bandage, if the case may be, or in direct contact with a wound. The absorption rate of the wrap must be high enough so as to prevent multiple replacement of the warp. The warp must also be conformable so a minimum of force is needed in the wrapping procedure. Although gauze is the most commonly used woven fabric in the medical industry, other woven material such as that described in the Secrist Patent No. 2,081,370, namely open meshed tobacco cloth or cheese cloth may also be used with equal results.

Six ply surgical wraps are presented as being presently used in the medical supply industry but are also being replaced by the present invention because the medical industry has determined that the present invention has more advantages and far exceeds any 6 ply fabric now being offered.

SUMMARY OF THE INVENTION

The present invention is an eight ply surgical wrap used for wrapping over and around a bandage to secure it in place, after it is applied to a patients limb. The wrap is free of exposed selvege edges and formed substantially of a single ply woven gauze fabric that is first bleached and washed and then folded into a four ply fabric and subjected to agitation in a hot water bath, and is passed through embossing rolls. The fabric is overfed into the hot water bath, which along with the hot water, agitation of the fabric and embossing, results in distorting the warp and filling yarns of the four ply fabric into an oblique and serpentine arrangement. The fabric is dried, wound and then the four ply fabric is folded to form an eight ply surgical wrap. The surgical warp not only is absorbent but due to its elastic properties, has the capability to elongate when being used as wrap around a bandage to more securely hold the bandage and it self in place.

Accordingly, it is the object to provide an improved surgical gauze wrap that is absorbent and has elastic properties.

It is also an object to provide a surgical wrap that overwhelmingly provides better services as any other surgical wrap but is more economical, due to the fact that less wrap has to be used to accomplish the same task as prior art.

It is a further object of the invention to reduce the time it takes a nurse or doctor to treat a patient.

Other objects of the invention will be apparent from the following description and drawings.

DESCRIPTION OF THE INVENTION

The creation of an eight ply surgical wrap was essentially caused by the present economic conditions. The present economic climate is such that in order to survive in the medical supply industry, a better and more efficient product had to be developed than was presently available in the market place. The medical supply industry is a very competitive industry and in anticipation of emergence into a health care program for the country, will become even more competitive in the future. Therefore, the present invention was born. The present invention not only improved the process time to make the fabric, but the additional plies made the fabric more absorbent, elastic and according to health care providers less fabric had to be used than what was previously necessary to accomplish the same purpose. The present invention has now been accepted as a replacement for 6 ply fabrics because its performance, as will be discussed, far exceeds the 6 ply. Furthermore, its use has reduced the amount of overwrap fabric that has to be used because it did not have to be changed as often. This also reduced the amount of time that has to be spent on a patient by a doctor or nurse, less changes of material, less time spent on patient. With these advantages more time could be spent for some other useful purpose. Other than the present invention, no one in the medical supply industry has even thought to improve the current prior art by increasing the plies to provide a more economical and competitive wrap.

This invention is a creation of necessity it was developed in order to continue to provide better products to the market place.

Figure 1:
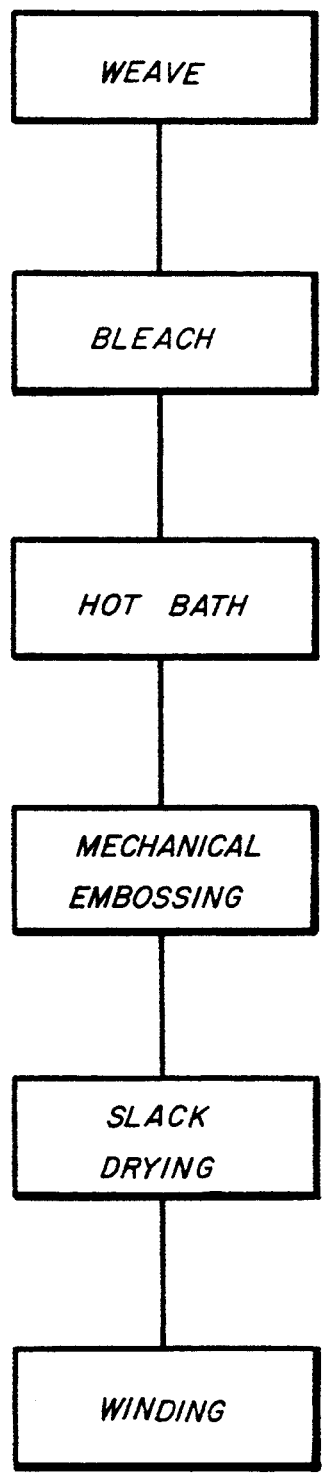
FIG. 1 is a schematic of a production line including a weaving machine, bleaching module, a hot water bath, a tension free dryer and a winder.
Figure 2:
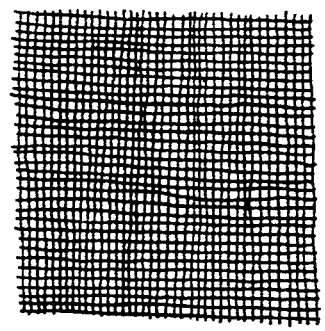
FIG. 2 is a plan view of a single sheet of a single ply fabric from which the surgical wraps of this invention are made.
Figure 4:
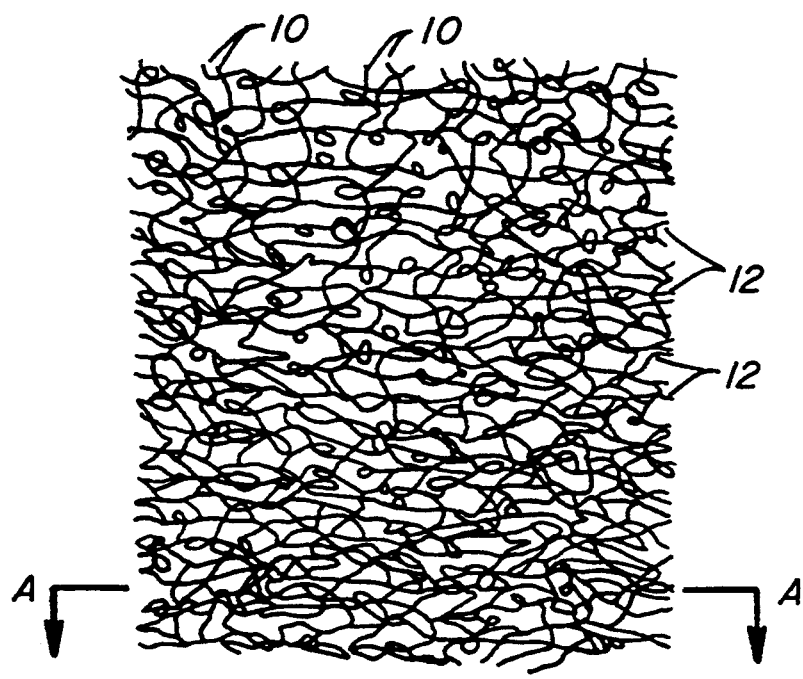
FIG. 4 is a plan view of the invention illustrating the arrangement of the yarns.
Figure 5:
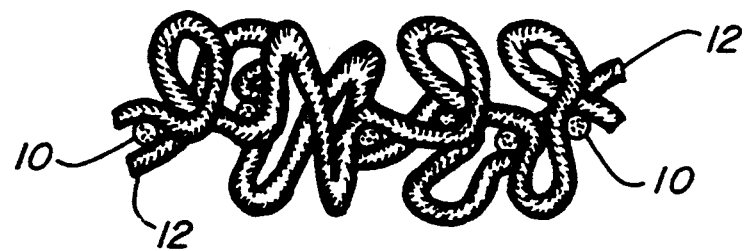
FIG. 5 is a cross-sectional view of the invention of FIG. 4 along the line A—A.

As shown in FIG. 1, the present invention is produced by weaving a single ply gauze fabric. The single ply fabric as illustrated in FIG. 2 has a warp yarn 10 and a fill yarn 12. The fabric is then processed according to FIG. 1. It is first purified by bleaching and washing it. After this process the single ply fabric is folded into a four ply fabric. After folding into a four ply fabric the fabric is overfed into a hot water bath and agitated and then passed through embossing rolls. The overfeeding, the hot water agitation of the fabric and the mechanical embossing cause the warp and fill yarns of the four ply fabric to become distorted into an oblique and serpentine arrangement, as shown in FIG. 4 and FIG. 5. The wet fabric is then removed from the water bath and dried without tension. Once dried the four ply fabric is folded into an eight ply fabric. The finished fabric is then wound, rolled and packaged into individual packages. The packaged fabric may then be sterilized if it is to be for medical purposes. The bleaching, washing and hot bath removes the surface coating of the yarns permitting them to become absorbent and fluffy, as well as making the material somewhat elastic. The yarns used in the fabric are 100% gauze.

Figure 3:
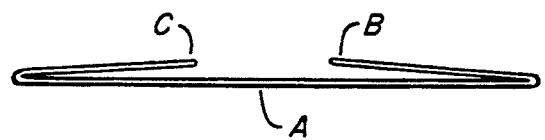
FIG. 3 is a plan view of a typical wrap of this invention illustrating the folding steps to create an eight ply wrap.
Figure 3:
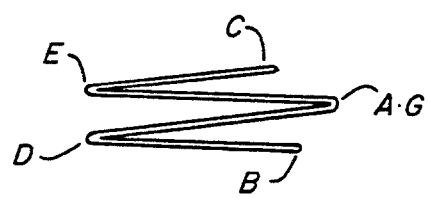
Figure 3:
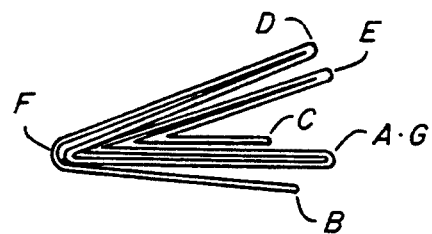

As a single fabric it is bleached and washed. After the wash the fabric is folded. As illustrated in FIG. 3, the steps taken in folding the single ply material to form a four ply material are as follow. The single ply material is folded inwardly from selvege edge B towards the center A of the fabric so selvege edge B is positioned approximately ⅜ of an inch left of the center A of the fabric, resulting in an edge D. Selvege edge C is then towards center A so selvege edge C is positioned approximately 1½ of an inch off the center A of the fabric, resulting in an edge E. Selvege edges B and C are folded at center A so they both appear on the same side of the fabric. The fabric is then folded at center A outwardly, in the opposite direction, so that edges D and E end up opposite each other, and as a result edge G is created. By folding in this manner a four ply fabric is achieved. And as earlier discussed this is the fabric that is subjected to the hot bath, agitation and embossing. After the fabric is dried it is then folded into an eight ply. This is accomplished by folding the four ply in the center, at F, so edge G of the fabric is folded inwardly towards E, resulting in edge C being positioned within the fold and B being positioned on the outside of the fold. This not only results in an eight ply fabric, but leaves selvege edges B and C in specific locations in from the edge of the fabric and separated from each other so they will not bind the fabric when used as a surgical wrap.

The material folded in this manner has no selvege edges positioned to bind around a limb when the material is wrapped around a bandage, nor will the edges of the material permit lint or fibers from the material causing foreign matter to invade otherwise sacrosanct wound coverings In addition, folding the material in this manner allows it to be significantly absorbent, fluffy, comfortable and elastic. Being absorbent and fluffy the material will absorb exude from wounds or prohibit exude from wicking through from a bandage to the surface of the wrap. Due to its elasticity or stretchability, the material has the capability to elongate when being used as wrap over and around a bandage to more securely hold the bandage and itself in place. And because it is comfortable, the wrap when used either as a wound covering or a support for a bandage, is not harsh. It also was unexpectedly found that the present invention eight ply wrap would absorb at least 33% more exude in a given area than a 6 ply fabric, thus, not permitting any exude to bleed through the wrap. The present invention also increased savings by medical personnel and more economical because a doctor or nurse does not have to change the wrap as many times as before or as called for by a 6 ply wrap. Therefore it is a time saver. In addition, 6 ply wraps have to use 2 wraps, or a combination of 12 plies, of the surgical material to accomplish what one wrap of an eight ply wrap will do. Because of the new structure, the process to make the eight ply become more economical because more material may be put through the process. The eight ply material is also made in shorter lengths, conserving material. An eight ply roll of wrap is 10 to 25% shorter in length than a 6 ply rolls. In addition to all the above advantages, the present invention provides substantially better coverage and protection than a 6 ply roll. The material is made with a thread count of 14±2 in the warp direction and 6.25±2 in the fill direction. In addition, the thread count per square inch of fabric is 20.2±3. The thread size is 31/1 in the warp direction and 35.6/1 in the fill direction. The fabric also has a stretch of 24±6%. The yarn used in the surgical wrap is 100% gauze.

The preferred process, once the weaving, bleaching and washing of the single ply fabric has taken place, is that process derived from the process set forth in Secrist U.S. Pat. No. 2,081,370, which describes a hot water bath. Although Secrist describes a bath for a single ply fabric our invention is folded into a four ply fabric prior to entering the hot bath, which permits more material to be processed and has a diffident effect on the fabric itself, as is described in the following sentence. After bleaching and washing the present invention fabric is overfed into the bath, agitated and subjected to embossing rolls so the yarns in the plies are more susceptible to entanglement, as shown in FIG. 5, into an oblique and serpentine arrangement.

Figure 6:
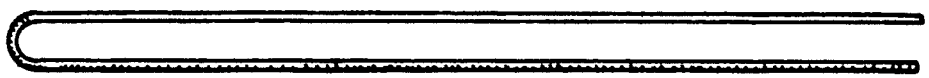
FIG. 6 is a view of the invention illustrating alternate folding steps to create an eight ply wrap.
Figure 6:
Figure 6:

In addition, as shown in FIG. 6 there is an alternate way to fold the present invention.

What is claimed is:

1. A process for producing an eight ply surgical wrap comprising, in order, the steps of:
   (1) weaving a single ply gauze fabric having a first and second selvege edge;
   (2) purifying the fabric by bleaching and washing the single woven gauze fabric;
   (3) folding the purified single ply fabric into a four ply fabric;
   (4) overfeeding the bleached and washed four ply fabric into a hot bath and while the fabric is in the hot bath mechanically embossing the fabric to cause the fabric warp and fill yarns to become distorted into an oblique and serpentine arrangement;
   (5) removing the fabric from the hot bath and drying the fabric without tension; and
   (6) folding the four ply fabric into an eight ply fabric.

2. A process as defined in claim 1 wherein the mechanical embossing comprises the step of passing the fabric through embossing rolls.

3. A process as defined in claim 1 including the step of rolling the eight ply fabric to provide a roll of the fabric.

4. A process as defined in claim 3 including the step of packaging the roll of fabric into individual packages.

5. A process as defined in claim 4 including the step of sterilizing the roll of fabric after it has been packaged.

* * * * *